(12) United States Patent
Seguin et al.

(10) Patent No.: US 10,406,300 B2
(45) Date of Patent: Sep. 10, 2019

(54) DUAL CHAMBER INHALER FOR SEQUENTIALLY ADMINISTERING MULTIPLE DRUGS

(71) Applicant: VAPOMED LIMITED, Nassau (BS)

(72) Inventors: Jacques Seguin, Launen (CH); Emad Sabry, La Croix-Sur-Lutry (CH)

(73) Assignee: Vapomed Limited, Nassau (BS)

( * ) Notice: Subject to any disclaimer, the term of this patent is extended or adjusted under 35 U.S.C. 154(b) by 494 days.

(21) Appl. No.: 15/241,030

(22) Filed: Aug. 18, 2016

(65) Prior Publication Data

US 2016/0354558 A1    Dec. 8, 2016

Related U.S. Application Data

(63) Continuation-in-part of application No. PCT/EP2016/052640, filed on Feb. 8, 2016.

(30) Foreign Application Priority Data

Feb. 6, 2015    (FR) ...................................... 15 50985

(51) Int. Cl.
  *A61M 11/00*    (2006.01)
  *A61K 45/06*    (2006.01)
  (Continued)

(52) U.S. Cl.
  CPC ........... *A61M 11/00* (2013.01); *A61K 9/0043* (2013.01); *A61K 9/0078* (2013.01);
  (Continued)

(58) Field of Classification Search
  CPC ....... A61B 5/0075; A61B 5/085; A61B 5/087; A61B 5/4839; A61K 2300/00;
  (Continued)

(56) References Cited

U.S. PATENT DOCUMENTS 4,464,378 A    8/1984   Hussain
4,950,237 A    8/1990   Henault et al.
(Continued)

FOREIGN PATENT DOCUMENTS

CN    102068697 B    10/2013
EP    1 370 212 A1   12/2003
(Continued)

OTHER PUBLICATIONS

Helmers, et al., Comparison of Intra-Venous and Intranasal Sufentanil Absorption and Sedation, Canadian Journal of Anesthesia, pp. 494-497 (1989).
(Continued)

*Primary Examiner* — Annette Dixon
(74) *Attorney, Agent, or Firm* — Foley & Lardner LLP; Christopher C. Bolten; Nicola A. Pisano

(57) ABSTRACT

Devices and methods for sequential aerosolized administration of pharmaceutical agents. A portable device may be used to administer an initial dose of an active formulation comprising at least one first pharmaceutical agent and a subsequent dose of an active formulation comprising at least one second pharmaceutical agent that may have the effect of countering, enhancing, or mitigating the first pharmaceutical agent.

22 Claims, 2 Drawing Sheets

(51) Int. Cl.
  A61K 31/135    (2006.01)
  A61K 31/4535   (2006.01)
  A61K 31/485    (2006.01)
  A61K 31/5517   (2006.01)
  A61M 15/08     (2006.01)
  A61K 9/00      (2006.01)
  A61M 31/00     (2006.01)
  A61M 39/22     (2006.01)
  A61M 16/00     (2006.01)

(52) U.S. Cl.
  CPC ........ *A61K 31/135* (2013.01); *A61K 31/4535* (2013.01); *A61K 31/485* (2013.01); *A61K 31/5517* (2013.01); *A61K 45/06* (2013.01); *A61M 15/08* (2013.01); *A61M 31/00* (2013.01); *A61M 39/22* (2013.01); *A61M 2016/0021* (2013.01); *A61M 2205/33* (2013.01); *A61M 2205/3334* (2013.01); *A61M 2205/3569* (2013.01); *A61M 2205/50* (2013.01); *A61M 2205/52* (2013.01); *A61M 2205/583* (2013.01); *A61M 2205/587* (2013.01); *A61M 2205/8206* (2013.01); *A61M 2205/8256* (2013.01); *A61M 2205/8262* (2013.01); *A61M 2210/0618* (2013.01); *A61M 2230/005* (2013.01); *A61M 2230/20* (2013.01); *A61M 2230/205* (2013.01); *A61M 2230/42* (2013.01); *A61M 2230/435* (2013.01)

(58) Field of Classification Search
  CPC .............. A61K 31/4745; A61K 31/485; A61K 31/5513; A61K 45/06; A61K 9/2009; A61K 9/2018; A61K 9/2054; A61K 9/2077; A61K 9/485; A61K 9/4858; A61K 9/4866; A61K 9/5078; A61K 9/5084; A61M 15/0003; A61M 15/0005; A61M 15/008; A61M 15/0083; A61M 15/009; A61M 16/0003; A61M 16/0051; A61M 16/024; A61M 16/08; A61M 16/10; A61M 16/104; A61M 16/12; A61M 16/14; A61M 2016/0027; A61M 2016/003; A61M 2016/0036; A61M 2021/0072; A61M 2202/0208; A61M 2202/0225; A61M 2202/0233; A61M 2202/025; A61M 2202/0291; A61M 2205/14; A61M 2205/3368; A61M 2205/3569; A61M 2205/3592; A61M 2205/505; A61M 2205/52; A61M 2205/6054; A61M 2205/6081; A61M 2205/8206; A61M 2205/8225; G05B 13/021; G05B 17/02; G06F 17/5009; G06F 2217/80
  See application file for complete search history.

(56) References Cited

U.S. PATENT DOCUMENTS

| | | |
|---|---|---|
| 4,969,579 A | 11/1990 | Behar |
| 5,512,578 A | 4/1996 | Crain et al. |
| 5,535,950 A | 7/1996 | Barriac et al. |
| 5,629,011 A | 5/1997 | Illum |
| 5,767,125 A | 6/1998 | Crain et al. |
| 5,767,215 A | 6/1998 | Garoff et al. |
| 6,098,620 A | 8/2000 | Lloyd et al. |
| 6,605,060 B1 | 8/2003 | O'Neil |
| 6,610,271 B2 | 8/2003 | Wermeling |
| 6,948,492 B2 | 9/2005 | Wermeling et al. |
| 7,875,001 B2 | 1/2011 | Minotti |
| 8,198,291 B2 | 6/2012 | Wermeling |
| 8,857,429 B2 * | 10/2014 | Spandorfer ......... A61M 15/009 128/203.14 |
| 8,987,290 B2 | 3/2015 | Woodward |
| 9,173,837 B2 | 11/2015 | Hillis et al. |
| 2003/0077300 A1 | 4/2003 | Wermeling |
| 2003/0191147 A1* | 10/2003 | Sherman ............ A61K 9/2009 514/282 |
| 2004/0068222 A1 | 4/2004 | Brian |
| 2004/0115133 A1 | 6/2004 | Wermeling |
| 2004/0129270 A1* | 7/2004 | Fishman ........... A61M 16/0051 128/204.18 |
| 2005/0126562 A1 | 6/2005 | Rabinowitz et al. |
| 2006/0130828 A1 | 6/2006 | Sexton et al. |
| 2006/0207596 A1 | 9/2006 | Lane |
| 2007/0043032 A1* | 2/2007 | Mainville .......... A61K 31/4745 514/221 |
| 2007/0186923 A1 | 8/2007 | Poutiatine et al. |
| 2010/0331354 A1 | 12/2010 | Wermeling |
| 2012/0187937 A1 | 7/2012 | Blake et al. |
| 2012/0270895 A1 | 10/2012 | Wermeling |
| 2013/0090594 A1 | 4/2013 | Palmer et al. |
| 2013/0172759 A1 | 7/2013 | Melker et al. |
| 2014/0099369 A1 | 4/2014 | Oshlack et al. |
| 2015/0000673 A1 | 1/2015 | Martin |
| 2017/0100333 A1 | 4/2017 | Seguin et al. |

FOREIGN PATENT DOCUMENTS

| | | |
|---|---|---|
| EP | 1 727 549 A1 | 12/2006 |
| WO | WO-96/40332 A1 | 12/1996 |
| WO | WO-01/58447 A1 | 8/2001 |
| WO | WO-2005/020906 A2 | 3/2005 |
| WO | WO-2008/027499 A2 | 3/2008 |
| WO | WO-2008/085765 A2 | 7/2008 |
| WO | WO-2009/021106 A1 | 2/2009 |
| WO | WO-2009/114740 A2 | 9/2009 |
| WO | WO-2012/024106 A2 | 2/2012 |
| WO | WO-2013/021186 A1 | 2/2013 |
| WO | WO-2016/124788 A1 | 8/2016 |

OTHER PUBLICATIONS

Intranasal Medications in the Prehospital Setting, Therapeutic Intranasal Drug Delivery, available at www.intranasal.net.
Lundeberg, et al., Aspects of Pharmacokinetics and Pharmacodynamics of Sufentanil in Pediatric Practice, Pediatric Anesthesia, (21):274-279 (2011).
Nielsen, et al., Intranasal Sufentanil/Ketamine Analgesia in Children, Pediatric Anesthesia, (2):170-80 (2014); (Abstract Only).
Wante, La voie intra nasale, available at https://www.chu-brugmann.be/fr/news/20121206-criticalday-wante.pdf.
Database WPI, XP002751415, Thomson Scientific, London, GB; AN 2011-H53355, CN102068697 A (Yichang Humanwell Pharm Co Ltd) May 25, 2011, Abstract.
International Search Report & Written Opinion dated Mar. 24, 2016 in Int'l PCT Patent Application Serial No. PCT/EP2016/052640.

* cited by examiner

DUAL CHAMBER INHALER FOR SEQUENTIALLY ADMINISTERING MULTIPLE DRUGS

I. CROSS-REFERENCE TO RELATED APPLICATIONS

This application is a continuation-in-part of International PCT Patent Application No. PCT/EP2016/052640, filed Feb. 8, 2016, which claims priority to FR Patent Application No. 1550985, filed Feb. 6, 2015, the entire contents of each of which are incorporated herein by reference.

II. TECHNICAL FIELD

The present disclosure relates to methods and apparatus for sequentially administering a first dose of a first pharmaceutical agent, and at a later time, a second dose of a second pharmaceutical agent to counteract or mitigate effects of the first dose. An exemplary embodiment is described for pain management involving sequential administration of active ingredients that may have side effects of respiratory depression, for example, opioid agonists and benzodiazepines.

III. BACKGROUND

Opioid agonists are used therapeutically for the treatment of pain, or during detoxification treatment as a replacement drug. Opioid agonists are substances which have effects similar to opium, but are not chemically related. Opioid agonists exert their effects by stimulating opioid receptors (also called opiate receptor). Three main types of opioid receptors include mu ($\mu$), delta ($\delta$) and kappa ($\kappa$). These opioid receptors are widely distributed in the brain and in some peripheral areas. The pharmacological response caused by complex opioid agonist/receptor formations depends on the type of opioid receptor being stimulated.

Commonly used opioid agonists include, but are not limited to, alfentanil, anileridine, apomorphine, buprenorphine, butorphanol, carfentanil, codeine, diamorphine ("heroin"), dextropropoxyphene, dihydromorphine, fentanyl, hydrocodone, hydromorphone, levallorphan, levophenacylmorphan, levorphanol, methadone, morphine, nalbuphine, nalorphine, norievophanoi, oxycodone, oxymorphone, pentazocine, pethidine, propoxyphene, remifentanil, sufentanil, tramadol, etc. In addition, a number of endogenous substances may be classified as opioid agonists such as dynorphins, endorphins, endorphins, enkephalins, nociceptors, etc.

Opioid agonists may have many undesirable side effects including drowsiness, respiratory depression, constipation, nausea, vomiting, etc. Accordingly, the use of opioid agonists should be handled with care, especially in the hospital or any health care setting. In addition, treatment with opioid agonists pose many risks of misuse as opioid agonists may be used as a substitute for hard drugs. As a result, supply clinics require expensive security systems for tracking and controlling such drugs. Finally, as opioid agonists may be highly addictive, increased dosages resulting from long-term treatment may cause the patient to become dependent, especially when the administration of the therapy is "on demand." Accordingly, an opioid agonist-based therapy requires strict regulation and strong involvement of medical staff, which is problematic in the context of cost optimization.

The administration of opioids predominantly involve injectable solutions, especially in the hospital environment. This form of administration has a number of advantages, for example, the effect is very fast and bioavailability is well controlled. However, administration by injection is has some drawbacks. For example, in addition to the discomfort of the injection and the requirement of a professional for administration, side effects may be very pronounced including, but not limited to, respiratory depression.

Opioid agonists may be associated with opioid antagonists in the case of opioid poisoning and/or to limit certain side effects. Opioid antagonists, in contrast to opioid agonists, are characterized by their inhibitory activity of at least one opioid receptor. Opioid antagonists may be divided into two main classes: specific opioid antagonists and non-specific opioid antagonists, e.g., naloxone, naltrexone, and nalmefene.

Another class of drugs used therapeutically includes benzodiazepines. Benzodiazepines are used primarily for their main properties: hypnotics, anxiolytics, anti epileptics, muscle relaxant, and amnesic.

Commonly used benzodiazepines include, but are not limited to, alprazolam, bromazepam, chlordiazepoxide, clobazam, clonazepam, clotiazepam, clorazepate, diazepam, estazolam, flunitrazepam, loprazolam, lorazepam, lormetazepam, midazolam, nitrazepam, nordazepam, oxazepam, prazepam, temazepam, tetrazepam, triazolam, etc.

Benzodiazepines may have many undesirable side effects including amnesia, abnormal behavior, tolerance, respiratory depression, etc. Benzodiazepines may be associated with a benzodiazepine antagonist, e.g., flumazenil, in the case of benzodiazepines poisoning or to limit certain side effects, e.g., respiratory depression. Benzodiazepine antagonists, unlike benzodiazepines, are characterized by their inhibitory activity of benzodiazepines.

Despite the strong need for treating pain with analgesic active ingredients such as opioid agonists and benzodiazepines, that need is limited by undesirable side effects, particularly respiratory depression. Specifically, regarding the public health, there is a need for reduced respiratory depression, limited misuse, and other to avoid other problems associated with addictive drugs. In addition, regarding ergonomics of treatment, there is a need for secure management made easier, noninvasive administration and limited post-treatment harm. Regarding the costs of using such drugs in treatment, there also is a need for limited intervention of the hospital staff, reduced hospitalization durations, reduced misuse impacting health systems, and reduced costs of distribution networks, among others.

In particular, there is a long felt need for a technical solution for delivering active ingredients for treating pain in an independently patient-controlled manner without any medical facility, while at the same time, managing the undesirable side effects of such treatment. This need especially concerns people including, for example, soldiers, journalists, adventurers, explorers, hunters, hikers, climbers, who may be far from any medical personnel or treatment center, e.g., hospital, clinic or health center. Indeed, these people are often found in places where the objective dangers involving the maintenance of bodily integrity are quite significant, and the risk of inflicting traumatic injury is high. Therefore there is a need for a single therapeutic solution for managing various situations of which there is a manifestation of pain through proper administration of suitable active pharmaceutical ingredients, while at the same time, avoiding undesirable side effects.

Various efforts have been made to improve opioid therapy, but satisfactory results have yet to be obtained. For example, Chinese application CN 102068697 describes combining an opioid agonist and an opioid antagonist in attempt to limit the adverse effects of the opioid agonist without impacting its effect. Specifically, the application teaches a nasal spray comprising a mixture of fentanyl/naltrexone. However, the application fails to describe limiting the number of administrations or controlling the potential side effects once the opioid antagonist metabolizes.

U.S. Patent Pub. No. 2007/0186923, assigned to AcelRx Pharmaceuticals, describes a medical delivery device for the administration of opioid agonists in the oral mucosa. The device has a safety component which prevents opioid antagonist spill when attempting to recover the opioid agonist solution. The application also describes a security system that ensures neutralization of the effect of the opioid agonist composition in case of attempted hijacking, making the composition unusable. Under normal conditions, no mixing occurs between the opioid agonist and the opioid antagonist, and no antagonist administration takes place.

WO 2012024106, assigned to the University of Florida, describes a complex system consisting of the acquisition of pharmacokinetic and pharmacodynamic data, and algorithmic analysis, wherein the response may be variable. The application specifies that the oximeter is not considered a reliable device for detecting abnormality, and that other probes are preferred. In addition, the device is not transportable.

WO 1996040332, assigned to Go Medical, describes a medical device for intranasal administration of an opioid agonist. The device includes a solution comprising an opioid agonist and other active molecules other than opioid antagonists. Thus, the application does not envisage the incorporation of opioid antagonists. In addition, the application fails to describe limiting misuse, and only describes a control system wherein a patient uses "good faith."

U.S. Pat. No. 4,464,378 to Hussain describes methods of intranasal administration of antagonists and corresponding formulations in, for example, gel form. The objective stated in that patent is to circumvent the difficulties encountered with the use of certain known products which have shown insufficient bioavailability during oral administration. That patent describes formulating solutions, gels, suspensions, and ointments containing the agonist-antagonist opioid for intranasal administration.

U.S. Pat. No. 5,629,011 to Ilium describes intranasal formulations of polar metabolites of opioid agonists in combination with an absorption promoter acting in the mucous membranes.

U.S. Pat. No. 5,767,125 to Crain describes a method of co-administration of an opioid agonist with an opioid antagonist. The opioid agonist is selected from morphine, codeine, fentanyl analogs, pentazocine, buprenorphine, methadone, enkephalins, dynorphins, endorphins, and alkaloids and opioid peptides which behave in the same way. The opioid antagonist is selected from naltrexone, naloxone, etorphine, diprenorphine, dihydroetorphine, and alkaloids, and opioid peptides behaving in the same way. The product is administered to mice by intraperitoneal injection, but the patent raises the possibility of preparing formulations for oral, sublingual, intravenous, intramuscular, subcutaneous, and transdermal administration.

WO 2001058447 to Oshlack describes compositions containing an opioid agonist and an opioid antagonist that may be formulated for intranasal administration. In this application, the opioid antagonist is coated with a substrate, e.g., a polysaccharide, to form microspheres to control its release on the mucous membranes so as to ensure the effect of the opioid antagonist during the administration.

U.S. Pat. No. 6,948,492 to Wermeling describes systems and intranasal delivery devices regarding controlling the minimum time between intranasal self-administration of a plurality of unit doses of a pharmaceutical composition. Unit doses contained in vials are deposited on a support star around a hub that may rotate to advance the unit dosage after each use, but only after a certain predetermined time has elapsed. The support star rotates and advances the vials, the progression of which is retained by a metal spring and a shape memory alloy wire. The locking is controlled by a microprocessor which counts down between each administration. The patent does not describe co-administering an opioid agonist and an opioid antagonist, or another form of control preventing the inappropriate administration of the composition. Indeed, although it is possible for the disclosed device to self-administer subsequent doses of opioid composition, the dosage is not in a physiological condition to withstand such administration.

As described above, efforts to improve opioid therapy include the administration of opioid agonists and opioid antagonists together in a single composition. However, devices made for simultaneous administration of opioid agonists and opioid antagonists prevents the opioid agonists from being fully effective prior to the mitigating effects of the opioid antagonists. For example, U.S. Pat. No. 7,875,001 to Minotti describes a nasal spray apparatus for simultaneously introducing at least two medicaments into a patient's nasal cavity. The medicaments are mixed prior to administration and are not administered individually and sequentially. Similarly, U.S. Patent App. No. 2006/0207596 to Lane describes a dual nasal applicator system for simultaneously delivering a first and second nasal drug composition housed in separate chambers wherein the first and second nasal drug compositions remain separated until dispensed into the patient's nasal cavity. The compositions are mixed either just prior to or during administration, and are not administered individually and sequentially.

In summary, none of the efforts mentioned above resolve the problems described above. As will be discussed below, devices and methods in accordance with the principles of the present disclosure solves the aforementioned problems.

IV. SUMMARY

The present disclosure overcomes the drawbacks of previously-known devices, systems, and methods of administration for the treatment of pain. The methods and apparatus of the present invention involve an aerosol administration device having at least two chambers for the sequential administration of at least a first pharmaceutical agent followed by at least a second pharmaceutical agent. For example, the first pharmaceutical agent may comprise an active formulation having at least one active ingredient selected from a drug group, whereas the second pharmaceutical agent may comprise an active formulation having at least one active ingredient selected from an antidote group.

In one exemplary embodiment constructed in accordance with the principles of the present invention, devices and methods are described for sequential aerosolized administration of at least two pharmaceutical agents, e.g., to manage pain. In accordance with one aspect of the present disclosure, a portable medical device for sequential aerosolized administration of at least a first pharmaceutical agent and at least a second pharmaceutical agent having an effect of countering, enhancing, or mitigating an effect of the first pharmaceutical agent is provided. The device may include a first chamber having a first sprayable active formulation disposed therein, wherein the first sprayable active formulation includes at least a first pharmaceutical agent having at least one active ingredient selected from a drug group. Drug groups may include, for example, opioid agonists and benzodiazepines. The device may further include a second chamber having a second sprayable active formulation disposed therein, wherein the second sprayable active formulation includes at least a second pharmaceutical agent having at least one active ingredient selected from an antidote group. Antidote groups may include, for example, opioid antagonists and benzodiazepine antagonists.

The device may also include a dispensing nozzle for permitting administration of the first sprayable active formulation and the second sprayable active formulation through a bodily tissue of a patient. The bodily tissue may be any tissue that may be reached by aerosolized administration of the pharmaceutical agents, i.e., nasal mucosa, buccal mucosa, rectal mucosa, bladder mucosa, vaginal mucosa, pulmonary tissue, lung tissue, etc. The dispensing nozzle may include, for example, a nosepiece. In addition, the device may include a valve chamber in communication with the first chamber, the second chamber, and the dispensing nozzle. The valve chamber may have a valve member for permitting communication between the first chamber or the second chamber, and the dispensing nozzle.

The device may permit an initial administration of the first sprayable active formulation. The device may further permit one or more subsequent administrations of the second sprayable active formulation or the first sprayable active formulation. For example, one of the one or more subsequent administrations may be of the second sprayable active formulation, and another one of the one or more subsequent administrations may be of the first sprayable active formulation. The first sprayable active formulation may also include at least one active ingredient selected from the antidote group, wherein the active ingredient from the antidote group of the first sprayable active formulation may be identical to the active ingredient from the antidote group of the second sprayable active formulation. Similarly, the second sprayable active formulation may also include at least one active ingredient selected from the drug group, wherein the active ingredient from the drug group of the second sprayable active formulation may be identical to the active ingredient from the drug group of the first sprayable active formulation.

The device may also include a signal processing unit operatively connected to the valve chamber, one or more sensors, one or more sensory alarms, and an actuator. The one or more sensors may measure data, and may include, for example, a timer, a flow sensor, and/or a device for measuring at least one biological parameter such as a respiratory rate sensor or an oximeter. The device for measuring at least one biological parameter may be positioned on the nosepiece of the dispensing nozzle.

Specifically, the timer may measure a time interval from the time of the measurement and a previous administration. The flow sensor may measure the amount of active formulation administered. Accordingly, the signal processing unit may also permit one or more subsequent administrations of a controlled dosage of the first sprayable active formulation or the second sprayable active formulation, having an amount of the second pharmaceutical agent sufficient to counter undesirable side effects induced by a previous administration of the first sprayable active formulation based on the amount measured by the flow sensor.

The signal processing unit may also include a memory for storing the measured data and/or predetermined threshold values. Accordingly, the signal processing unit may also perform one or more comparisons between the measured data and the predetermined threshold values. The one or more sensory alarms may, based on the one or more comparisons, communicate to a patient one or more signals indicative of whether the valve member is positioned to permit communication between the first chamber or second chamber, and the dispensing nozzle. For example, the one or more sensory alarms may include a device that emits light. The signal processing unit also may be programmed to selectively inhibit dispensing from either the first chamber or the second chamber.

The actuator may be activated by the patient based on the one or more signals to cause the signal processing unit to permit administration of the first sprayable active formulation or the second sprayable active formulation. The device may also include a power source configured to provide energy to the device.

In accordance with another aspect of the present disclosure, a method for sequential aerosolized administration of at least two pharmaceutical agents for the treatment of pain is provided. The method includes administering an initial dose of the first sprayable active formulation alone through a bodily tissue of a patient, wherein the first sprayable active formulation comprises at least a first pharmaceutical agent, and administering a subsequent dose of the second sprayable active formulation alone through the bodily tissue of the patient, wherein the second sprayable active formulation comprises at least a second pharmaceutical agent having an effect of countering, enhancing, or mitigating an effect of the first pharmaceutical agent. The method may further include administering a subsequent dose of the first sprayable active formulation alone through the bodily tissue of the patient prior to the administration of the subsequent dose of the second sprayable active formulation.

V. BRIEF DESCRIPTION OF THE DRAWINGS

VI. DETAILED DESCRIPTION

Figure 1:
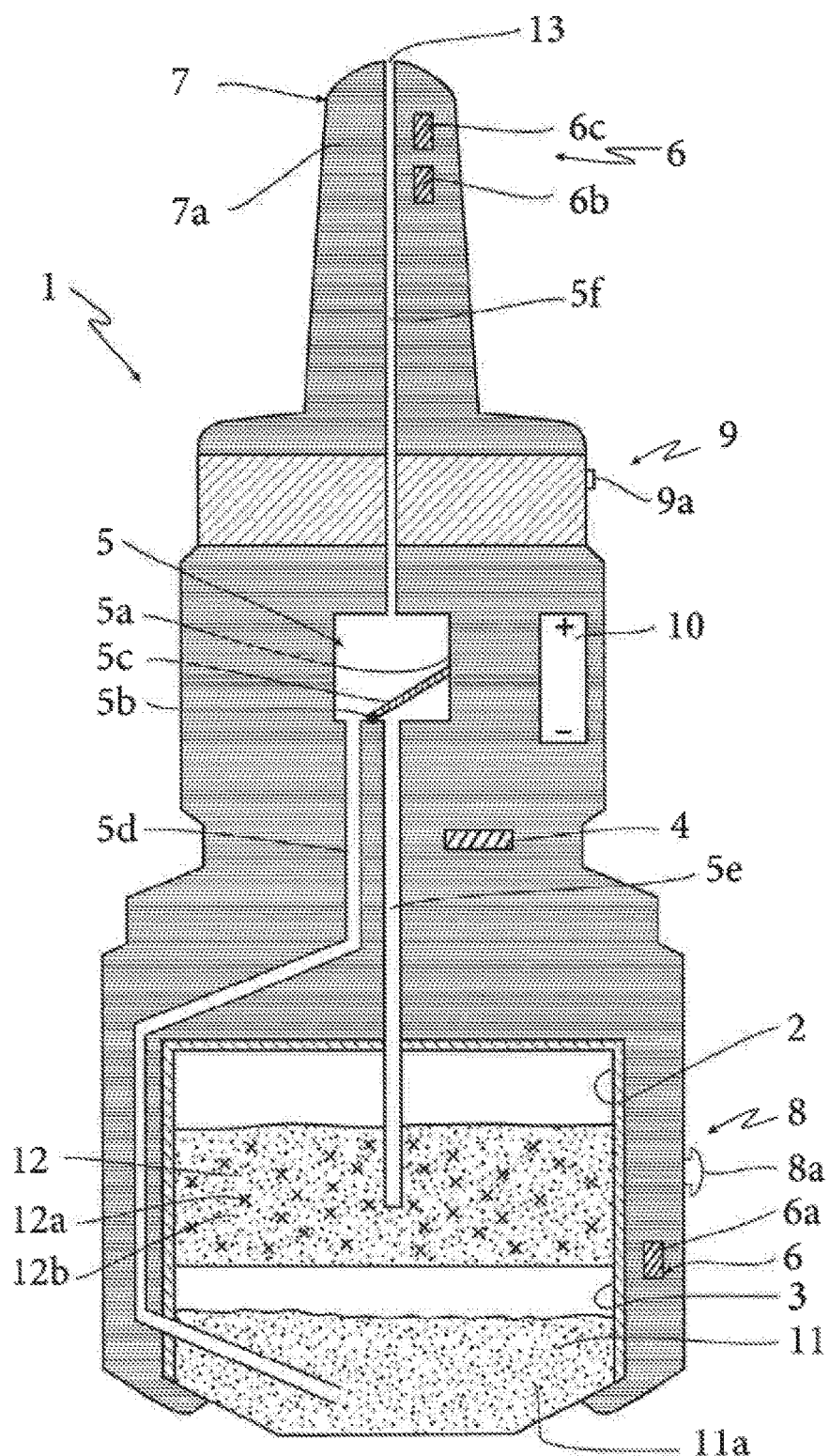
FIG. 1 illustrates a portable device for sequential intranasal administration in accordance with the principles of the present invention.

Devices and methods of the present disclosure comprise a portable aerosol administration device having at least two chambers for the sequential administration of at least a first pharmaceutical agent followed by at least a second pharmaceutical agent. For example, in an exemplary embodiment, the first pharmaceutical agent may comprise an active formulation having at least one active ingredient selected from a drug group, whereas the second pharmaceutical agent may comprise an active formulation having at least one active ingredient selected from an antidote group. Alternatively, the pharmaceutical agents may comprise, for example, a drug and a complementary drug, a drug and a drug activator, etc. In accordance with the principles of the present disclosure, the device may be optimized for aerosolized administration through a bodily tissue. For example, the device may be optimized for aerosolized administration through any bodily tissue that may be reached by aerosol administration, e.g., buccal mucosa, rectal mucosa, bladder mucosa, vaginal mucosa, pulmonary tissue, lung tissue, etc. As detailed herein, in an exemplary embodiment, the device may have two chambers and may be a nasal inhalator for sequential aerosolized administration of two pharmaceutical agents through the nasal mucosa.

In the context of this application, "active ingredients selected from a drug group" refers to active ingredients having at least one side effect, e.g., respiratory depression. For example, drug groups may include opioid agonists and benzodiazepines.

In the context of this application, "active ingredients selected from an antidote group" refers to active ingredients that have an effect of countering at least one side effect, e.g., respiratory depression, induced by the active ingredient selected from the drug group. For example, antidote groups may include opioid antagonists and benzodiazepine antagonists.

Unless otherwise defined, each technical or scientific term used herein has the same meaning as commonly understood by one of ordinary skill in the art to which this disclosure belongs. In accordance with the claims that follow and the disclosure provided herein, the following terms are defined with the following meanings, unless explicitly stated otherwise.

"Undesirable side effect" is an effect following the administration of an active ingredient that it is not directly desired. Undesirable side effects may be limited by the administration of a particular amount of active ingredients selected from the antidote group that have an effect of countering the undesirable side effect.

"Respiratory depression" is an undesirable side effect following the administration of at least one active ingredient selected from the drug group. Symptoms of respiratory depression include, for example, hypoxia, increased carbon dioxide levels in the breath, reduced oxygen levels in the breath, decreased respiratory rate, decreased breathing amplitude, etc.

"Excessive respiratory depression" is a state of respiratory depression wherein the risk/benefit of simultaneous administration of at least one active ingredient from the drug group and at least one active ingredient from the antidote group is not desirable. For example, when the measured biological parameter is oxygen saturation, respiratory depression may be considered excessive when the oxygen saturation value is lower than 85%. In addition, when the biological parameter is the respiratory rate, respiratory depression may be considered excessive when the value of the respiratory rate is less than 12 inspiration/expiration cycles per minute.

"Active formulation" is a formulation comprising one or more active pharmaceutical ingredients, e.g., pharmaceutical agents. The active ingredients may be formulated as a solution or a non-molecular dispersion. The active ingredients may also be formulated in a form such that its properties are modified, particularly those properties related to the passage of membranes and bioavailability, e.g., microcapsules, liposomes, fast acting forms, etc. "Active formulation," "active pharmaceutical ingredients," "active ingredients," and "pharmaceutical agents" are used synonymously and interchangeably throughout the specification.

"Aerosolized administration" is the administration of the active formulation(s) in aerosol form, e.g., a suspension of fine solid particles or liquid droplets in air or another gas, wherein the particles fall under 50 cm per second.

"Intranasal administration" is the administration of an active formulation in the patient's nasal cavity, such that the active ingredients may be absorbed by the nasal mucosa. The active ingredients may be administered in various forms including gas, steam, microdroplets, suspended powder, etc.

"Buccal administration" is the administration of an active formulation in the patient's buccal cavity, such that the active ingredients may be absorbed by the buccal mucosa.

"Rectal administration" is the administration of an active formulation in the patient's rectal cavity, such that the active ingredients may be absorbed by the rectal mucosa.

"Intravaginal administration" is the administration of an active formulation in the patient's vaginal cavity, such that the active ingredients may be absorbed by the vaginal mucosa.

"Sequential administration" is the administration of one or more subsequent doses of the active formulation(s).

"Independent administration" is when the aerosolized administration is performed by the patient himself or herself, without the intervention/supervision of a health professional. When the administration takes place in an animal, the administration is performed by the breeder or owner.

"Administration without any medical facility" means that the aerosolized administration of the active formulation(s) may take place without any intervention/supervision of a health professional. Optionally, the aerosolized treatment may be prescribed by a health professional, while the administration itself takes place in an environment where such health professionals are neither present nor necessary.

“initial stage” is the time period during which an initial administration of an active formulation is performed.

“Subsequent stage” refers to the time period after the initial administration during which any subsequent administration of the same or different active formulation is performed.

“Administration simultaneously/simultaneous administration” is the simultaneous administration of at least two active ingredients. The at least two active ingredients may be formulated as an active formulation mixture disposed in a single chamber. Alternatively, each active ingredient may be administered separately, but their pharmacological effects begin at the same time and/or are generally simultaneous.

“Choice of administration” is when the patient elects to receive an administration of a particular active formulation.

“Biological parameter” refers to a patient’s biological characteristic, which may be in the form of a numerical physiological value where quantifiable. For example, biological parameters may include oxygen saturation and/or respiratory rate.

“Device for measuring at least one biological parameter” is a device that produces a numerical value corresponding to a biological parameter of the patient.

“Device for measuring at least one biological parameter introduced concomitantly” is when at least a portion of a device for measuring at least one biological parameter is positioned in communication with the bodily tissue during at least the beginning of the aerosolized administration.

“Liquid spray” is a liquid capable of being transformed into droplets and/or microdroplets.

“Mixture of active ingredients” is the presence of multiple active ingredients within a single chamber. The mixture may be formulated as a liquid, solid, or gas. In a gas mixture, molecules of different active ingredients may be dispersed within the same chamber called a molecular mixture.

“Initial actuation” refers to the first operation of the administration of therapy by the patient. There may only be one initial actuation during a single therapy.

“Subsequent actuation” refers to any subsequent operation of the administration of therapy by the patient after the initial actuation. There may be one or more subsequent actuations during a single therapy.

"Removable chamber" is a chamber that may be removed from the device without rendering the device permanently unusable.

"Changeable chamber" is a chamber that may be removed and replaced with a new chamber including, where appropriate, the same active formulation.

Referring now to FIG. 1, portable device 1 for intranasal administration may include first chamber 2, second chamber 3, signal processing unit 4, valve chamber 5, sensors 6, dispensing nozzle 7, actuator 8, sensory alarm 9, and autonomous power source 10. Portable device 1 may be used for independent administration by the patient, and not as a burden that limits the mobility of device 1. In particular, device 1 may be so easily transported that a mere possibility of having to use it, e.g., in an emergency, justifies its portability. For example, device 1 may be sized and shaped to fit in a pocket, a hand, a bag, a box car glove, a handbag, a capsule resistant to water and/or sand, etc.

First and second chambers 2 and 3 may be an enclosed space configured to contain an active formulation. For example, first chamber 2 may contain first active formulation 12. As shown in FIG. 1, first active formulation 12 may comprise active ingredient 12a selected from a drug group, and active ingredient 12b selected from an antidote group. Second chamber 3 may contain second active formulation 11. As shown in FIG. 1, second active formulation 11 may comprise active ingredient 11a selected from an antidote group. However, as will be understood by one of ordinary skill in the art, first active formulation 12 and second active formulation 11 may comprise any suitable combination of active pharmaceutical ingredients in accordance with the principles of the present disclosure.

For example, first active formulation 12 may comprise at least one active ingredient selected from the drug group, alone or in combination with at least one active ingredient selected from the antidote group. Second active formulation 11 may comprise at least one active ingredient selected from the antidote group, alone or in combination with at least one active ingredient selected from the drug group. In addition, at least one active ingredient selected from the drug group in first active formulation 12 may be identical to at least one active ingredient selected from the drug group in second active formulation 11, and/or at least one active ingredient selected from the antidote group in first active formulation 12 may be identical to at least one active ingredient selected from the antidote group in second active formulation 11. Alternatively, at least one active ingredient selected from the drug group in first active formulation 12 may be different from at least one active ingredient selected from the drug group in second active formulation 11, and/or at least one active ingredient selected from the antidote group in first active formulation 12 may be different from at least one active ingredient selected from the antidote group in second active formulation 11. In addition, at least one of the active formulations may comprise at least one active pharmaceutical ingredient having the effect of modifying the passage properties of membranes and bioavailability.

In addition, first and second chambers 2 and 3 may be enclosed such that air exchange with the outside is low or nonexistent. During operation of device 1, the enclosed space of first chamber 2 and second chamber 3 may communicate with the outside through valve chamber 5 and dispensing nozzle 7.

Signal processing unit 4 is a module that may be operatively connected to valve chamber 5, sensors 6, actuator 8, and/or sensory alarm 9. For example, sensors 6 may measure and transmit information to signal processing unit 4 where the information is evaluated, e.g., compared with a threshold value. Signal processing unit 4 may further include a memory configured to store predetermined threshold values and/or the measured values received from sensors 6. Signal processing unit 4 may then direct valve chamber 5 to position valve member 5c such that dispensing nozzle 7 may be in communication with the appropriate chamber. Signal processing unit 4 may then direct sensory alarm 9 to transmit a signal the patient so the patient may make a choice of administration. The patient may, based on the signal, activate actuator 8, e.g., push button 8a, which causes signal processing unit 4 to issue operation control signals to permit the administration of an active formulation. The administration of the active formulation may be carried out by dispensing mechanisms commonly known in the art for aerosolized administration devices, e.g., a positive displacement pump, a piston, etc.

Valve chamber 5 is a space in device 1 and may comprise dosage chamber 5a, valve member 5c, ducts 5d and 5e in communication with first and second chambers 2 and 3, respectively, and duct 5f in communication with outlet 13 of device 1. Valve member 5c may be configured to permit administration of an active formulation from chamber 2 or chamber 3, through outlet 13 of dispensing nozzle 7. Valve member 5c may be a mechanical barrier, e.g., a valve. Valve member 5c may be configured to rotate about valve axis 5b based upon the active formulation desired to be administered. For example, valve member 5c may be positioned against either side wall of dosage chamber 5a to permit communication between first chamber 2 or second chamber 3, and outlet 13. As shown in FIG. 1, valve member 5c is positioned against a side wall of dosage chamber 5a such that communication is closed between first chamber 2 and outlet 13, and communication is only permitted between second chamber 3 and outlet 13 via duct 5d and duct 5f. As such, active formulation 11 may be administered from chamber 3 of device 1 through, for example, the nasal mucosa via duct 5d, valve chamber 5, duct 5f, and outlet 13 upon activation of actuator 8.

Sensors 6 may include one or more devices configured to acquire and transmit data indicative of which active formulation should be administered and in what amount. Sensors 6 may comprise at least one of timer 6a, one or more flow sensors, or a device for measuring at least one biological parameter, e.g., respiratory rate sensor 6b or oximeter 6c. The biological parameter measured may be selected from at least one of oxygen saturation, intranasal rate of oxygen exhale, intranasal rate of carbon dioxide exhaled, respiratory rate, or any combination thereof, e.g., both oxygen saturation and respiratory rate.

Timer 6a is a device configured to measure a time interval elapsed since a previous administration of an active formulation. Timer 6a may include, for example, a clock, a stopwatch, a countdown timer, a microprocessor operating at a known frequency operation, etc. Alternatively, signal processing unit 4 may include a clock, e.g., a PSTN circuit, or other timer integrated therewith, e.g., on a microprocessor of signal processing unit 4, to avoid providing a separate clock. The one or more flow sensors may be configured to measure an amount of active formulation administered. The one or more flow sensors may be positioned anywhere along the path of communication between first and second chambers 2 and 3, and dispensing nozzle 7, e.g., within dosage chamber 5a, and/or ducts 5d, 5e, or 5f. Respiratory rate sensor 6b and oximeter 6c may be configured to measure biological parameters, e.g., respiratory rate and oxygen saturation, and determine corresponding numerical values.

Dispensing nozzle 7 is a portion of device 1 having outlet 11, and configured for transmission of active formulations through the nasal mucosa. Dispensing nozzle 7 may be sized and shaped to be comfortably inserted in a patient's nasal cavity, e.g., nosepiece 7a. As such, respiratory rate sensor 6b and oximeter 6c may be positioned on nosepiece 7a of device 1 such that respiratory rate sensor 6b and oximeter 6c may acquire measurements concomitantly with the introduction of dispensing nozzle 7 into the patient's nasal cavity.

Actuator 8 may be any device capable of receiving a mechanical stress, e.g., pushbutton 8a, voice activated device, etc.

Sensory alarm 9 may include one or more devices configured to emit a signal perceptible by the patient, thereby allowing the patient to obtain information effecting the choice of the administration. For example, sensory alarm 9 may include light 9a. Light 9a is configured to emit a light observable by the patient. The patient may, at any time, obtain information indicative of which active formulation would be administered via sensory alarm 9 by actuating sensors 6, e.g., inserting respiratory rate sensor 6b and/or oximeter 6c into the nasal cavity. The patient may then decide whether to activate actuator 8.

Autonomous power source 10 is an independent energy source that may supply electric current to device 1 to permit the independent administration of the active formulation(s). Power source 10 may generally be portable, and preferably incorporated into device 1. Power source 10 may be, for example, a rechargeable battery, a source of photovoltaic energy, a capacitor, a source of solar energy, energy recovered from the patient, e.g., heat generated by motion, etc.

Figure 2:
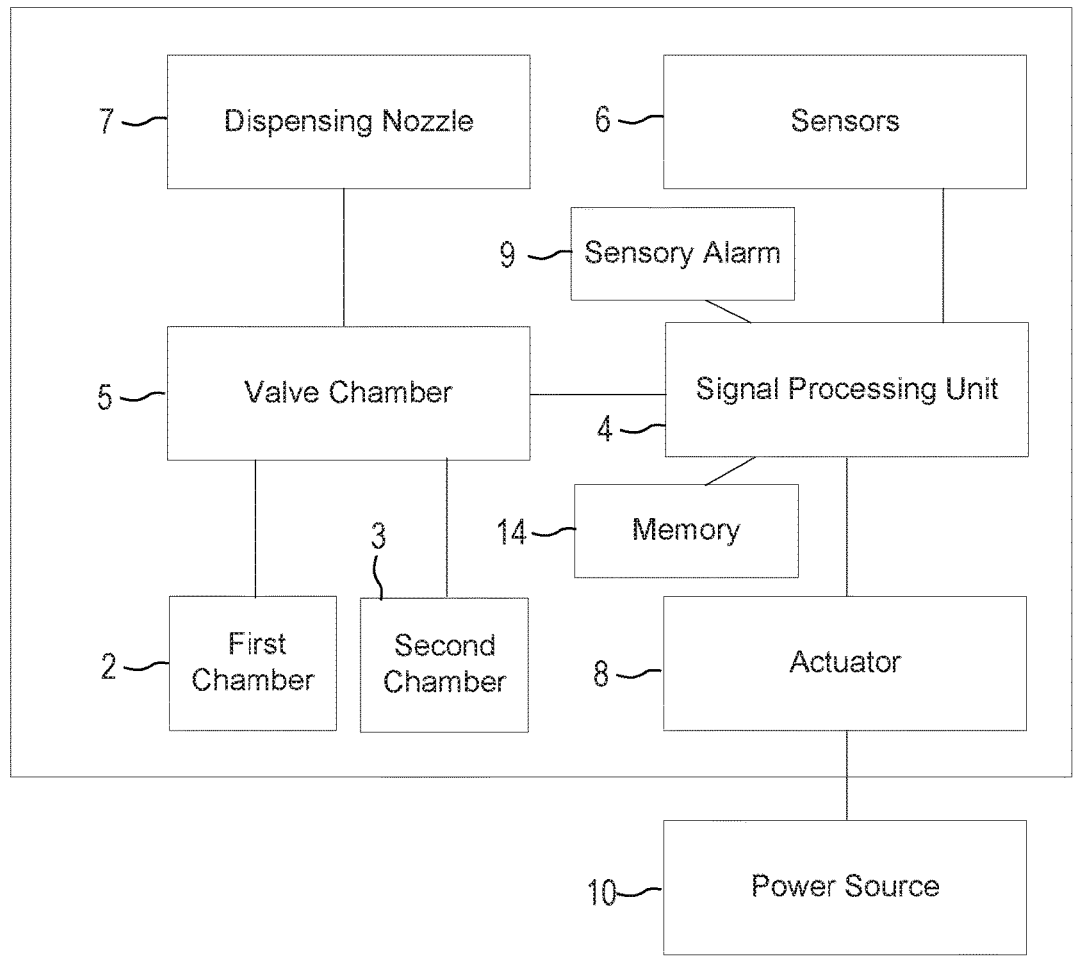
FIG. 2 is a schematic block diagram illustrating various features of the device of FIG. 1 in accordance with the principles of the present invention.

Referring now to FIG. 2, a schematic block diagram illustrating various features of device 1 in accordance with the principles of the present disclosure is provided. As shown in FIG. 2, signal processing unit 4 may be operatively connected to valve chamber 5, sensors 6, actuator 8, and sensory alarm 9. In addition, valve chamber 5 may be in communication with first and second chambers 2 and 3, and dispensing nozzle 7.

Device 1 may be used for independent administration by a patient for managing pain. For example, device 1 may likely be used by people who are in isolated situations as described above. To operate device 1, the patient may quickly retrieve device 1 from, for example, a backpack, or its optional case. The patient then positions dispensing nozzle 7, e.g., nosepiece 7a within the patient's nasal cavity and activates actuator 8 to administer an initial dose of an active formulation having at least one active ingredient from the drug group. After some time, the patient may reinsert nosepiece 7a within the patient's nasal cavity. Sensors 6 may measure at least one biological parameter and may provide the measured data, e.g., time interval since last administration, oxygen saturation, amount of active formulation administered, and/or respiratory rate, to signal processing unit 4.

Signal processing unit 4 may also be operatively connected to memory 14 configured to store data received from sensors 6. Signal processing unit 4, upon receiving the data from the one or more devices for measuring at least one biological parameter, e.g., respiratory rate sensor 6b and/or oximeter 6c, and/or the flow sensor, may interrogate timer 6a to calculate a current time value. Timer 6a may then send the time value to signal processing unit 4 for storage in memory 14.

Signal processing unit 4 may perform a comparison between the physiological value obtained from the one or more devices for measuring at least one biological parameter, and a threshold value stored in memory 14, and/or signal processing unit 4 may perform a comparison between the time elapsed since the previous administration, e.g., difference between time value stored in memory 14 and an updated time value received from timer 6a at the time of the comparison, and a threshold value stored in memory 14. Signal processing unit 4 may send a signal to valve chamber 5 and sensory alarm 9 to enable the patient to activate actuator 8 to self-administer the appropriate active formulation based on the results of the comparisons.

For example, if signal processing unit 4 determines that the physiological value exceeds a threshold value stored in memory 14, and/or that sufficient time has elapsed since the previous administration, e.g., exceeds a threshold value, signal processing unit 4 may send a signal to valve member 5 to permit communication between chamber 2 and dispensing nozzle 7, such that activation of actuator 8 permits a subsequent administration of first active formulation 12 having at least one active ingredient from the drug group. First active formulation 12 may also include at least one active ingredient from the antidote group in combination with the at least one active ingredient from the drug group, such that the at least one active ingredient from the antidote group and the at least one active ingredient from the drug group are in a mixture.

Alternatively, if signal processing unit 4 determines that the physiological value is less than a threshold value stored in memory 14, e.g., excessive respiratory depression, and/or that an insufficient time interval has elapsed since the previous administration, e.g, lower than a threshold value, signal processing unit 4 may send a signal to valve chamber 5 to permit communication between chamber 3 and dispensing nozzle 7, such that activation of actuator 8 permits a subsequent administration of second active formulation 11 having at least one active ingredient from the antidote group. In addition, based on the measured data received from the flow sensor indicative of the amount of active formulation previously administered, e.g., active formulation having at least one active ingredient from the drug group, signal processing unit 4 may permit a subsequent administration of a controlled amount of second active formulation 11 having an amount of at least one active ingredient from the antidote group sufficient to counter the undesirable side effects induced by the previous administration of the active formulation having at least one active ingredient from the drug group upon activation of actuator 8. As such, the patient would not receive too little or too much of the active ingredient from the antidote group.

The threshold value of timer 6a may be, for example, between 1 and 10 hours, between 4 and 8 hours, or about 6 hours. When the biological parameter being measured is oxygen saturation, the threshold value of the measurement of the oxygen saturation may be, for example, between 70 and 90%, between 80 and 90%, or about 85%. When the biological parameter being measured is respiratory rate, the threshold value of the measured respiratory rate may be, for example, between 8 and 14 cycles/minute, between 8 and 12 cycles/minute, or about 12 cycles/minute.

Signal processing unit 4 may also direct sensory alarm 9, e.g., light 9a, to communicate a signal to the patient indicating which of the two active formulations would be administered upon the activation of actuator 8. For example, when the signal is positive, e.g., light 9a emits a light, the signal may indicate that an active formulation containing at least one active ingredient from the drug group, with or without an active ingredient from the antidote group, may be issued. When the signal is negative, e.g., light 9a does not emit a light or light 9a emits a light having a color different from that of a positive signal, it may indicate that an active formulation containing at least one active ingredient from the antidote group, but no active ingredients from the drug group may be issued. For example, sensory alarm 9 will transmit a negative signal to the patient when at least one of sensors 6 transmits information to signal processing unit 4 causing valve member 5c to prevent communication between the chamber containing an active formulation comprising at least one active ingredient from the drug group with or without any active ingredients from the antidote group, e.g., first chamber 2, and dispensing nozzle 7.

Based on the signal from sensory alarm 9, the patient may activate actuator 8, e.g., pushbutton 8a, for self-administration of the appropriate active formulation without any assistance from a medical professional. When the patient activates actuator 8, signal processing unit 4, based on the information provided by sensors 6, controls communication via valve chamber 5 between either first chamber 2 or second chamber 3, and outlet 13.

First chamber 2 may contain first sprayable active formulation 12 comprising at least one active ingredient 12a from a drug group, and second chamber 3 may contain second sprayable active formulation 11 comprising at least one active ingredient 11a from an antidote group. As described above, one of ordinary skill in the art would understand that first active formulation 12 and second active formulation 11 may comprise any suitable combination of active pharmaceutical ingredients in accordance with the principles of the present disclosure as described above. Each of chambers 2 and 3 may be removable, and/or changeable. The initial actuation of device 1 may comprise of administration of active formulation 11 alone, and the one or more subsequent actuations of device 1 may comprise of administration of active formulation 11 alone or active formulation 12 alone.

The patient may, as part of the therapy, perform as many intranasal administrations as desired. Although this therapy may be an "on demand" therapy, it is completely safe and secure. Accordingly, device 1 may simplify difficult situations, especially in the context of use during armed conflict, natural disasters, etc.

Autonomous power source 10 may supply power, e.g., electric power, to device 1.

Device 1 may incorporate multiple active formulations, e.g., active formulations 11 and 12, the qualitative and quantitative compositions of each of which may be adapted for a given patient. The active formulations may be in the form of sprayable liquid, e.g., vaporized liquid. The choice of dosage as well as which active ingredients form the active formulations may be at the discretion of a medical personnel. The time interval threshold value, e.g., minimum duration between administrations of the active formulations, calculated by the timer 6a, e.g., clock, and/or biological parameter threshold values may be predetermined by the medical personnel.

With respect to the doses of active ingredients from the drug and antidote groups described below, all doses were estimated for patients of average weight, e.g., about 70 kg. Such doses may be adjusted, especially for patients of different weights, as is well known in the art. The doses may also be adapted for specific animals.

The following doses may be applied to the devices and methods of administration of active formulations for use in the treatment of pain in accordance with the principles of the present disclosure.

In one embodiment, at least one active ingredient from the drug group consists of opioid agonists, and at least one active ingredient from the antidote group consists of opioid antagonists. For example, at least one active ingredient from the drug group may be selected from the group consisting of alfentanil, anileridine, apomorphine, buprenorphine, butorphanol, carfentanil, codeine, diamorphine ("heroin"), dextropropoxyphene, dihydromorphine, fentanyl, hydrocodone, hydromorphone, levallorphan, levophenacylmorphan, levorphanol, methadone, morphine, nalbuphine, nalorphine, norlevophanol, oxycodone, oxymorphone, pentazocine, pethidine, propoxyphene, remifentanil, sufentanil, tramadol, etc. The at least one active ingredient from the drug group may also be selected from the group consisting of sufentanil, fentanyl, diamorphine, buprenorphine, and carfentanil. At least one active ingredient from the antidote group may be selected from the group consisting of naloxone and naltrexone.

At least one active ingredient from the drug group may be sufentanil, and at least one active ingredient from the antidote group may be naloxone. For example, when the dose of sufentanil is between 2 and 50 µg the dose of naloxone may be between 2 and 50 mg; when the dose of sufentanil is between 5 and 30 µg the dose of naloxone may be between 5 and 30 mg; when the dose of sufentanil is between 10 and 20 µg the dose of naloxone may be between 10 and 20 mg; when the dose of sufentanil is between 17 and 50 µg the dose of naloxone may be between 17 and 50 mg, when the dose of sufentanil is 10 µg the dose of naloxone may be 10 mg; when the dose of sufentanil is 15 µg the dose of naloxone may be 15 mg; and when the dose of sufentanil is 20 µg the dose of naloxone may be 20 mg.

The weight ratio of sufentanil and naloxone may be between 0.00004 and 0.025. Alternatively, the weight ratio of sufentanil and naloxone may be about 0.001.

At least one active ingredient from the drug group may be sufentanil, and at least one active ingredient from the antidote group may be naloxone, such that any administration of sufentanil may be accompanied by the simultaneous administration of ketamine. For example, when the dose of sufentanil is between 1 and 60 µg, the dose of ketamine may be between 1 and 60 mg, and the dose of naloxone may be between 1 and 60 mg; when the dose of sufentanil is between 10 and 55 µg, the dose of ketamine may be between 10 and 55 mg, and the dose of naloxone may be between 10 and 55 mg; when the dose of sufentanil is between 17 and 50 µg, the dose of ketamine may be between 17 and 50 mg, and the dose of naloxone may be between 17 and 50 mg; when the dose of sufentanil is between 17 and 50 µg the dose of ketamine may be between 17 and 50 mg, and the dose of naloxone may be between 17 and 50 mg; when the dose of sufentanil is 17 µg the dose of ketamine may be 17 mg, and the dose of naloxone may be 17 mg; when the dose of sufentanil dose is 37.5 µg the dose of ketamine may be 37.5 mg, and the dose of naloxone may be 37.5 mg; and when the dose of sufentanil dose is 50 µg the dose of ketamine may be 50 mg, and the dose of naloxone may be 50 mg. An active formulation may comprise of sufentanil, naloxone, and ketamine in a mixture.

The weight ratio of sufentanil and naloxone, and the weight ratio of ketamine and naloxone may be, respectively, between 0.00034 and 0.0029, and between 0.34 and 2.9. Alternatively, the weight ratio of sufentanil and naloxone ratio may be about 0.001, and the weight ratio of ketamine and naloxone ratio may be about 1.

At least one active ingredient from the drug group may be fentanyl, and at least one active ingredient from the antidote group may be naloxone. For example, when the dose of fentanyl is between 10 and 150 µg the dose of naloxone may be between 2 and 50 mg; when the dose of fentanyl is between 30 and 120 µg the dose of naloxone may be between 5 and 30 mg; when the dose of fentanyl is between 50 and 100 µg the dose of naloxone may be between 10 and 20 mg; when the dose of fentanyl is 50 µg the dose of naloxone may be 10 mg; when the dose of fentanyl is 75 µg the dose of naloxone may be 15 mg; and when the dose of fentanyl is 100 the dose of naloxone may be 20 mg.

The weight ratio of fentanyl and naloxone may be between 0.0002 and 0.075. Alternatively, the weight ratio of fentanyl and naloxone ratio may be about 0.005.

At least one active ingredient from the drug group may be diamorphine, and at least one active ingredient from the antidote group may be naloxone. For example, when the dose of diamorphine is between 0.1 and 20 mg, the dose of naloxone may be between 2 and 50 mg; when the dose of diamorphine is between 1 and 10 mg, the dose of naloxone may be between 5 and 30 mg; when the dose of diamorphine is between 2 and 4 mg, the dose of naloxone may be between 10 and 20 mg; when the dose of diamorphine is 2 mg, the dose of naloxone may be 10 mg; when the dose of diamorphine is 3 mg, the dose of naloxone may be 15 mg; and when the dose of diamorphine is 4 mg, the dose of naloxone may be 20 mg.

The weight ratio of diamorphine and naloxone may be between 0.02 and 10. Alternatively, the weight ratio of diamorphine and naloxone may be about 0.2.

At least one active ingredient from the drug group may be buprenorphine, and at least one active ingredient from the antidote group may be naloxone. For example, when the dose of buprenorphine is between 0.1 and 30 mg, the dose of naloxone may be between 0.1 and 5 mg, when the dose of buprenorphine is between 1 and 15 mg, the dose of naloxone may be between 0.3 and 3 mg; when the dose of buprenorphine is between 2 and 8 mg, the dose of naloxone may be between 0.5 and 2 mg; when the dose of buprenorphine is 2 mg, the dose of naloxone may be 0.5 mg; when the dose of buprenorphine is 4 mg, the dose of naloxone may be 1 mg; when the dose of buprenorphine is 6 mg, the dose of naloxone may be 1.5 mg; and when the dose of buprenorphine is 8 mg, the dose of naloxone may be 2 mg.

The weight ratio of buprenorphine and naloxone may be between 0.02 and 300. Alternatively, the weight ratio of buprenorphine and naloxone may be about 4.

At least one active ingredient from the drug group may be carfentanil, and at least one active ingredient from the antidote group may be naloxone. For example, when the dose of carfentanil is between 70 and 1900 µg, the dose of naloxone may be between 0.3 and 3.7 mg; when the dose of carfentanil is between 140 and 1400 µg, the dose of naloxone may be between 0.5 and 3.0 mg; when the dose of carfentanil is between 350 and 1000 µg, the dose of naloxone may be between 0.7 and 2.0 mg; when the dose of carfentanil is 350 µg, the dose of naloxone may be 0.70 mg; when the dose of carfentanil is 700 µg, the dose of naloxone may be 1.4 mg; and when the dose of carfentanil is 1000 µg, the dose of naloxone may be 2 mg.

The weight ratio of carfentanil and naloxone may be between 0.019 and 6.6. Alternatively, the weight ratio of carfentanil and naloxone may be about 0.5.

When the active formulation contains no active ingredient from the drug group, at least one active ingredient from the antidote group may be naloxone, wherein the dose of naloxone may be between 1 and 40 mg, or between 5 and 20 mg.

When the at least one active ingredient from the drug group is buprenorphine and the active formulation contains no active ingredient from the drug group, at least one active ingredient from the antidote group may be naloxone, wherein the dose of naloxone may be between 3 to 7 mg.

In one embodiment, at least one active ingredient from the drug group consists of benzodiazepines and at least one active ingredient from the antidote group consists of benzodiazepines antagonists. For example, at least one active ingredient from the drug group may be selected from the group consisting of lorazepam, midazolam and flunitrazepam, and at least one active ingredient from the antidote group may be flumazenil. Alternatively, the active ingredients from the drug group may be lorazepam, and the active ingredients from the antidote group may be flumazenil. The dose of lorazepam may be between 2 and 5 mg.

At least one active ingredient from the drug group may be midazolam, and at least one active ingredient from the antidote group may be flumazenil, wherein the dose of midazolam may be between 3.5 and 10 mg.

At least one active ingredient from the drug group may be flunitrazepam, and at least one active ingredient from the antidote group may be flumazenil, wherein the dose of flunitrazepam may be between 2 and 10 mg.

When the active formulation contains no active ingredient from the drug group, at least one active ingredient from the antidote group may be flumazenil, wherein the dose of flumazenil may be between 0.1 and 1 mg, or between 0.6 and 1 mg.

When the active formulation contains at least one active ingredient from the drug group and no active ingredient from the antidote group, at least one active ingredient from the drug group may be selected from benzodiazepines.

When the active formulation comprises at least one active ingredient selected from a group consisting of lorazepam, midazolam, and flunitrazepam, the active formulation may not include flumazenil.

In addition, at least one of the active formulations may comprise at least one active pharmaceutical ingredient configured to modify the passage properties of membranes and bioavailability.

The following example illustrates a particular use of device 1 in accordance with the principles of the present disclosure. For example, device 1 may comprise removable first chamber 2 and removable second chamber 3. First chamber 2 may have first active formulation 12 disposed therein:

| active formulation 12 as a solution (10 mL) |
| --- |
| 1875 µg sufentanil<br>1875 mg ketamine<br>1875 mg naloxone<br>water and/or excipients (qs 100%) |

Second chamber 3 may have second active formulation 11 disposed therein:

| active formulation 11 as a solution (10 mL) |
| --- |
| 750 mg naloxone<br>water and/or excipients (qs 100%) |

The amount of active formulation used in each dose may be 0.2 mL, thus active formulation 12 may comprise about 50 doses: sufentanil (37.5 µg/dose)/ketamine (37.5 mg/dose)/naloxone (37.5 mg/dose), and active formulation 11 may comprise about 50 doses: naloxone (15 mg/dose).

Device 1 also may include one or more devices for measuring biological parameters: oximeter 6c (threshold value: 85% oxygen saturation), and respiratory rate sensor 6b (threshold value: 12 inspirations/expirations cycles per minute); timer 6a, e.g., clock (threshold value: 6 hours); and light 9a. When one of the threshold values of oximeter sensor 6c, respiratory rate 6b, or clock 6a are in favor of a re-administration of an active ingredient from the drug group, e.g., sufentanil, light 9a may emit a light on device 1, observable by the patient. Accordingly, the patient will know which active formulation will be administered upon activation of actuator 8 based on the light emitted by light 9a. As a result, the patient may then make a decision whether or not to activate actuator 8.

The following example illustrates a particular method of using device 1 in accordance with the principles of the present disclosure. For example, at T=0, the patient, without any medical facility, activates actuator 8 of device 1 for the first time, thereby administering active formulation 12. At T=3 hours, the patient introduces nosepiece 7a of device 1 into the patient's nasal cavity. After about 20 seconds, sensory alarm 9 emits a negative signal, indicating that the clock (and potentially the biological parameters) prohibits the subsequent administration of active formulation 12. Thus, the patient has the choice of whether or not to perform a subsequent administration of active formulation 11. At T=6.1 hours, the patient introduces nosepiece 7a of device 1 into the patient's nasal cavity. After about 20 seconds, sensory alarm 9 emits a negative signal, indicating that at least one of its two biological parameters, e.g., oxygen saturation and respiratory rate, prohibits the administration of active formulation 12. Again, the patient has the choice of whether or not to perform a subsequent administration of active formulation 11. At T=8 hours, the patient introduces nosepiece 7a of device 1 into the patient's nasal cavity. After about 20 seconds, sensory alarm 9 emits a positive signal, e.g., light 9a emits a light observable by the patient, indicating that active formulation 12 may be administered. Thus, the patient may choose whether or not to perform a subsequent administration of active formulation 12.

Although aspects of the present disclosure have been described in detail by way of illustration and example for purposes of clarity of understanding, it is readily apparent to those of ordinary skill in the art in light of the teachings of the present disclosure that certain changes and modifications may be made thereto without departing from the spirit or scope of the appended claims. Accordingly, the preceding merely illustrates the principles of embodiments of the present disclosure. For example, the device described above may have more than two chambers and may be optimized for sequential aerosolized administration of more than two pharmaceutical agents, e.g., a drug and an antidote, a drug and a complementary drug, a drug and a drug activator, etc., through other bodily tissues, e.g., buccal mucosa, rectal mucosa, bladder mucosa, vaginal mucosa, pulmonary tissue, lung tissue, etc.

What is claimed:

1. A portable medical device for sequential aerosolized administration of at least two pharmaceutical agents, the device comprising:
  a first chamber configured to have a first sprayable active formulation disposed therein, the first sprayable active formulation comprising a first pharmaceutical agent;
  a second chamber configured to have a second sprayable active formulation disposed therein, the second sprayable active formulation comprising a second pharmaceutical agent having an effect of countering, enhancing, or mitigating an effect of the first pharmaceutical agent;
  a dispensing nozzle configured to permit an initial administration of the first sprayable active formulation, the dispensing nozzle further configured to permit one or more subsequent administrations of the second sprayable active formulation through a bodily tissue; and
  a valve chamber in communication with the first chamber, the second chamber, and the dispensing, nozzle, the valve chamber having a valve member configured to move between a first position where the valve member only permits communication between the first chamber and the dispensing nozzle, and a second position where the valve member only permits communication between the second chamber and the dispensing nozzle.

2. The device of claim 1, wherein the first sprayable active formulation comprises a first pharmaceutical agent having at least one active ingredient selected from a drug group, and wherein the second sprayable active formulation comprises a second pharmaceutical agent having at least one active ingredient selected from an antidote group.

3. The device of claim 2, wherein the first sprayable active formulation comprises a first pharmaceutical agent having at least one active ingredient selected from a drug group comprising opioid agonists, and wherein the second sprayable active formulation comprises a second pharmaceutical agent having at least one active ingredient selected from an antidote group comprising opioid antagonists.

4. The device of claim 2, wherein the first sprayable active formulation comprises a first pharmaceutical agent having at least one active ingredient selected from a drug group comprising benzodiazepines, and wherein the second sprayable active formulation comprises a second pharmaceutical agent having at least one active ingredient selected from an antidote group comprising benzodiazepine antagonists.

5. The device of claim 1, wherein the first sprayable active formulation further comprises a second pharmaceutical agent having an effect of countering, enhancing, or mitigating an effect of the first pharmaceutical agent.

6. The device of claim 5, wherein the second pharmaceutical agent of the first sprayable active formulation is identical to the second pharmaceutical agent of the second sprayable active formulation.

7. The device of claim 1, wherein the second sprayable active formulation further comprises a first pharmaceutical agent.

8. The device of claim 7, wherein the first pharmaceutical agent of the second sprayable active formulation is identical to the first pharmaceutical agent of the first sprayable active formulation.

9. The device of claim 1, wherein the dispensing nozzle is configured to permit the initial and one or more subsequent, administrations of the first and second active formulations through the bodily tissue comprising at least one of a nasal mucosa, a buccal mucosa, a rectal mucosa, a bladder mucosa, a vaginal mucosa, a lung tissue, or a pulmonary tissue.

10. The device of claim 1, further comprising:
  a signal processing unit operatively connected to the valve chamber;
  one or more sensors operatively connected to the signal processing unit, the one or more sensors configured to measure data;
  one or more sensory alarms operatively connected to the signal processing unit, the one or more sensory alarms configured to communicate to a patient one or more signals indicative of whether the valve member is positioned to permit communication between the first chamber or second chamber, and the dispensing nozzle, based on the measured data;

an actuator operatively connected to the signal processing unit, the actuator configured to be activated by the patient, based on the one or more signals, to cause the signal processing unit to permit administration of the first sprayable active formulation or the second sprayable active formulation; and a power source configured to provide energy to the device.

11. The device of claim 10, wherein the signal processing unit further comprises a memory configured to store at least one of the measured data or predetermined threshold values.

12. The device of claim 11, wherein the signal processing unit is further configured to perform one or more comparisons between the measured data and the predetermined threshold values, and wherein the one or more sensory alarms are configured to communicate one or more signals indicative of whether the valve member is positioned to permit the administration of the first sprayable active formulation or the second sprayable active formulation, based on the one or more comparisons.

13. The device of claim 10, wherein at least one of the one or more sensors comprises a timer configured to measure a time interval elapsed from the time of the data measurement and a previous administration.

14. The device of claim 10, wherein at least one of the one or mor sensors comprises a flow sensor configured to measure an amount of active formulation administered.

15. The device of claim 14, wherein the signal processing unit is further configured to permit one or more subsequent administrations of a controlled dosage of the second sprayable active formulation having an amount of the second pharmaceutical agent sufficient to counter undesirable side effects induced by a previous administration of the first sprayable active formulation based, on the amount measured by the flow sensor.

16. The device of claim 10, wherein at least one of the one or more sensors comprises a device configured to measure at least one biological parameter.

17. The device of claim 16, wherein the device configured to measure at least one biological parameter comprises at least one of an oximeter or a respiratory rate sensor.

18. The device of claim 16, wherein the device configured to measure at least one biological parameter is configured to be positioned on the dispensing nozzle.

19. The device of claim 10, wherein at least one of the one or more sensory alarms comprises a device configured to emit light.

20. A method for sequential aerosolized administration of at least two pharmaceutical agents for the treatment of pain, the method comprising:

selecting a portable device for sequential aerosolized administration of at least two pharmaceutical agents for the treatment of pain, the device comprising a first chamber having a first sprayable formulation disposed therein, a second chamber having a second sprayable formulation disposed therein, a dispensing nozzle configured to permit administration of the first sprayable formulation and the second sprayable formulation, and a valve chamber in communication with the first chamber, the second chamber, and the dispensing nozzle, the valve chamber having a valve member configured to permit communication between the first chamber or the second chamber, and the dispensing nozzle;

administering an initial dose of the first sprayable active formulation alone through a bodily tissue of a patient, the first sprayable active formulation comprising a first pharmaceutical agent; and administering a subsequent dose of the second sprayable active formulation alone through the bodily tissue of the patient, the second sprayable active formulation comprising a second pharmaceutical agent having an effect of countering, enhancing, or mitigating an effect of the first pharmaceutical agent;

wherein the first and second sprayable active formulations are not co-administered simultaneously.

21. The method of claim 20, further comprising administering a subsequent dose of the first sprayable active formulation alone through the bodily tissue of the patient prior to the administration of the subsequent dose of the second sprayable active formulation.

22. The method of claim 20, wherein the portable device for sequential aerosolized administration of at least two active formulations further comprises a signal processing, unit having a memory, the signal processing unit operatively connected to the valve chamber, one or more sensors, an actuator, and one or more sensory alarms, the signal processing unit configured to:

receive measured data indicative of at least one of a time interval since a previous administration, an amount of active formulation administered, or a biological parameter from the one or more sensors;

compare the measured data to a predetermined threshold value stored in the memory;

actuate the valve chamber to position the valve member to permit communication between the first chamber or the second chamber, and the dispensing nozzle based on the comparison;

direct the one or more sensory alarms to communicate one or more signals to the patient based on the comparison; and permit administration of the first sprayable active formulation the sewn sprayable active formulation upon activation of the actuator by the patient based on the one or more signals.

* * * * *